United States Patent [19]
Kok et al.

[11] Patent Number: 6,100,241
[45] Date of Patent: *Aug. 8, 2000

[54] COCCIDIOSIS POULTRY VACCINE

[75] Inventors: Jacobus Johannes Kok, Nijmegen; Paul van den Boogaart, SC Oss; Arnodus Nicolaas Vermeulen, Cuyk, all of Netherlands

[73] Assignee: Akzo Nobel, N.V., Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/676,882

[22] Filed: Jul. 3, 1996

[30] Foreign Application Priority Data

Jul. 3, 1995 [EP] European Pat. Off. ............... 95201801

[51] Int. Cl.⁷ ..................... A01N 43/04; A61K 31/70; C12N 15/63; C12N 15/00
[52] U.S. Cl. .................. 514/44; 435/455; 435/320.1; 435/325; 435/456; 435/69.1; 435/70.1; 424/93.2; 536/23.1
[58] Field of Search ............................. 514/44; 424/93.2; 435/455, 320.1, 325, 456, 69.1, 70.1

[56] References Cited

FOREIGN PATENT DOCUMENTS 0223710  5/1987  European Pat. Off. .
0344808  12/1989  European Pat. Off. .
WO 9204460  3/1992  WIPO .

OTHER PUBLICATIONS

M. Wisher, *Molecular and Biochemical Parasitology*, 21:7–15, 1986.
Vermeulen et al., *FEMS Microbiology Letters*, 110:2:223–230, Jun. 15, 1993.
Blau et al (Nov. 2, 1995) New Eng. J. Med. 1204–1207.
Lazar et al (1998) Mole. Cell. Biol. 8, 1247–1252.
Burgess et al (1990) J. Cell Biol. 111, 2129–2138.
Jolley etal (1990) Immunol. 2, 329–339.
Hunt et al (1988) J. Virol. 8, 3014–3019.
Cantello et al (1991) j. Virol. 3, 1584–1588.
Taylor et al (1990) J. Virol. 4, 1441–1450.
Breed et al (1996) In Avian Diseases, Chapter 2, Immunity to *Eimeria tenella* in chickens: phenotypical and functional changes in peripheral blood T–cell subsets, agpes 37–48.
Finkelstein et al (1989) Tibtech. 7,273–277.
Sheppard et al (1989) Austral. Vet. J. 12, 421–423.
Tomley (1991) Vaccine 9,4–5.

*Primary Examiner*—Deborah Crouch
*Assistant Examiner*—Jill D. Martin
*Attorney, Agent, or Firm*—Mary E. Gormley

[57] ABSTRACT

This invention relates to Eimeria proteins with immunogenic properties as well as to DNA sequences encoding these proteins. These proteins can be administered to poultry thereby protecting the birds against coccidiosis. In addition the DNA encoding these proteins can be used for the preparation of a vector vaccine against coccidiosis.

25 Claims, 2 Drawing Sheets

COCCIDIOSIS POULTRY VACCINE

FIELD OF THE INVENTION

The present invention relates to a protein derived from *Eimeria acervulina*, which is capable of stimulating immune lymphocytes. It also relates to a nucleic acid sequence encoding all or an antigenically significant part of this protein, a recombinant vector comprising such a nucleic acid sequence, a host cell or organism transformed with such a recombinant vector and a vaccine for the protection of poultry against coccidiosis.

BACKGROUND OF THE INVENTION

Coccidiosis is a disease caused by infection with one or more of the many species of coccidia, intracellular protozoal parasites of the subphylum Apicomplexa and the genus Eimeria. Poultry is defined herein as domesticated birds that serve as a source of eggs or meat and that include such commercially important kinds as chickens, turkeys, ducks, geese, guinea fowl, pheasants, pigeons and peafowl.

Coccidiosis in chickens is known to be caused by several different species of Eimeria, namely *Eimeria acervulina, E. maxima, E. tenella, E. necatrix, E. brunetti, E. mitis, E. praecox, E. mivati* and *E. hagani*. Some people, however, doubt the true existence of the last two species. Low level infection with any of these Eimeria species results in a protective immunity to reinfection.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

*E. acervulina* is one of the most common species found in the litter of broiler houses in both Europe and the USA. It has a great reproductive potential and is regarded as pathogenic because it produces a marked depression in gain of body weight, higher feed conversion and it produces gross lesions in the upper small intestine.

During the life cycle (see also Table 1), the Eimeria parasite passes through a number of stages. The life cycle begins when the chicken ingests the infectious stage, known as the sporulated oocyst, during ground feeding or by inhalation of dust. The wall of the sporulated oocyst is ruptured by a combination of mechanical grinding action and chemical action in the gizzard and intestinal tract, resulting in the release of four sporocysts. The sporocysts pass into the duodenum where they are exposed to bile and digestive enzymes resulting in the release of two sporozites per sporocyst.

TABLE 1

Endogenous stages of *Eimeria acervulina* in stained sections of infected duodenum (after McDonald V. et al., Parasitol. 8, 21–30, 1982).

| Time of infection | Histological observations |
| --- | --- |
| 24 h | Immature $1^{st}$ generation asexual stages |
| 36 h | Semi-mature $1^{st}$ generation schizonts |
| 42 h | Mature $1^{st}$ gen. schizonts. Immature $2^{nd}$ gen. parasites |

TABLE 1-continued

Endogenous stages of *Eimeria acervulina* in stained sections of infected duodenum (after McDonald V. et al., Parasitol. 8, 21–30, 1982).

| Time of infection | Histological observations |
| --- | --- |
| 48 h | Mature $2^{nd}$ gen. schizonts. A few $3^{rd}$ gen. schizonts with 8–16 merozoites |
| 60 h | Mature $3^{rd}$ gen. schizonts, immature $4^{th}$ gen. parasites |

The sporozoites are mobile and search for suitable host epithelium cells in order to penetrate and reproduce in them. Following infection of an epithelium cell, the parasite enters the schizont phase of its life cycle, producing from 8 to 16 to >200 merozoites per schizont. Once released from the schizont, the merozoites are free to infect further epithelium cells. After from two to five of these asexual reproduction cycles, the intracellular merozoites grow into sexual forms known as the female or macrogametocyte and the male or microgametocyte. Following fertilization of the macrogametocyte by the microgametes released from the microgametocyte, a zygote is formed which creates a cyst wall about itself. The newly formed oocyst is passed out of the infected chicken with the droppings.

With the correct environmental conditions of temperature and humidity and sufficient oxygen in the air, the oocyst will sporulate into the infectious stage, ready to infect a new host and thereby spreading the disease. Thus no intermediate host is required for transfer of the parasite from bird to bird.

The result of the Eimeria parasite infecting the digestive tract of a chicken may be a reduction in weight gain, increased feed conversion, cessation of egg production and, in some cases, death. The increase in intensive production of poultry has been accompanied by severe losses due to this parasite; indeed, coccidiosis has become the most economically important parasitic disease. In the Netherlands, the losses that poultry farmers suffer every year run into millions of guilders; in 1986 the loss was about 13 million guilders. In the same year, a loss of 300 million dollars was suffered in the United States.

In the past, several methods have been used in attempts to control coccidiosis. Prior to the advent of chemotherapeutic agents, improved sanitation using disinfectants, together with the mechanical removal of litter, was the main method employed; sufficient oocysts, however, usually remained to transmit the disease.

The introduction of coccidiostatic agents in the feed or drinking water, in addition to good management, resulted in some success at disease control. Such agents have been found to suffer from a drop in effectiveness over the years, due partly to the development of drug resistant strains of coccidia. Furthermore, several chemotherapeutic agents have been found to leave residues in the meat, making it unsuitable for consumption.

Attempts have been made to control the disease immunologically by administering to chickens a live vaccine comprising oocysts from all seven species of Eimeria, the oocysts administered being from precocious lines. Such precocious lines are obtained by inoculating chickens with a wild population of an Eimeria species and collecting the very first parasites that are excreted as a result of the infection. The collected parasites are put back into chickens and the cycle is repeated several times. Eventually a precocious line of parasite is produced which has fewer cycles of asexual reproduction in the gut. Thus such lines retain their immunogenicity, whilst producing fewer parasites in the gut with less consequential damage being caused to the host chicken. The disadvantage of this type of vaccine is that it is expensive to produce because of the necessity of producing it in live chickens and its lower reproductive potential.

The advent of genetic engineering has provided new methods for producing effective vaccines. Using these methods, the DNA coding for the antigenic proteins of some pathogenic microorganisms has been cloned into such host microorganisms as *Escherichia coli* or Salmonella spec., with the result that the protein has been expressed at sufficiently high levels such that it can be incorporated into a vaccine. The advantage of proteins produced in this way is that they are noninfectious and are relatively cheap to produce. In this way, vaccines have been prepared against a number of viruses such as hepatitis, herpes simplex and foot and mouth disease.

Attempts have been made to genetically engineer a coccidiosis vaccine. European patent application No. 337 589 describes the isolation of a Group B *Eimeria tenella* protein and its insertion into a novel expression vector which, in turn, has been used to transform appropriate hosts. Patent Cooperation Treaty Application WO 92/04461 describes the construction of a microorganism that produces an antigenic protein using either the "mRNA route" or the "nuclear DNA route". In this way, certain antigens from *E. tenella* and *E. maxima* were prepared and sequenced. Taking this type of route to prepare antigens for incorporation into a vaccine relies only upon selecting antigens which could induce antibodies in an heterologous species. This approach does not necessarily end up with selecting the most protective antigen.

From H. S. Lillehoj (Vet. Immunol. Immunopath., 13, 321–330, 1986) it can be conceived that development of protective immunity in chickens infected with coccidia may be due to the development of a species-specific T cell response.

SUMMARY OF THE INVENTION

It has now been found that a very immunogenic protein can be isolated from the 42hr developmental stage of *Eimeria schizonts*. Surprisingly, this protein is found intracellularly in Eimeria and it appears to contain high sequence homology with known heterologous lactate dehydrogenases (LDH).

Thus, the invention provides a protein having one or more immunoreactive and/or antigenic determinants of Eimeria lactate dehydrogenase, which has a monomeric molecular weight of about 37 kD.

More specifically the lactate hydrogenase is derived from *Eimeria acervulina*.

According to a second aspect of the invention, there is provided a nucleic acid sequence encoding all or a substantial part, in particular the immunologically active part, of a purified Eimeria lactate dehydrogenase. Such a nucleic acid sequence may be operatively linked to expression control sequences resulting in a recombinant nucleic acid molecule which, when inserted into a suitable vector, results in a recombinant vector capable of expressing the nucleic acid sequence.

Such a recombinant vector, or nucleic acid sequence as defined above, may be used to transform a suitable host cell or organism. Such a transformed host cell or organism may, in turn, be used to produce the stimulatory protein for incorporation into a vaccine for the protection of poultry against coccidiosis. Alternatively, the transformed host cell or organism may its elf be incorporated into a vaccine.

DETAILED DESCRIPTION OF THE INVENTION

Figures 1A, 1B:
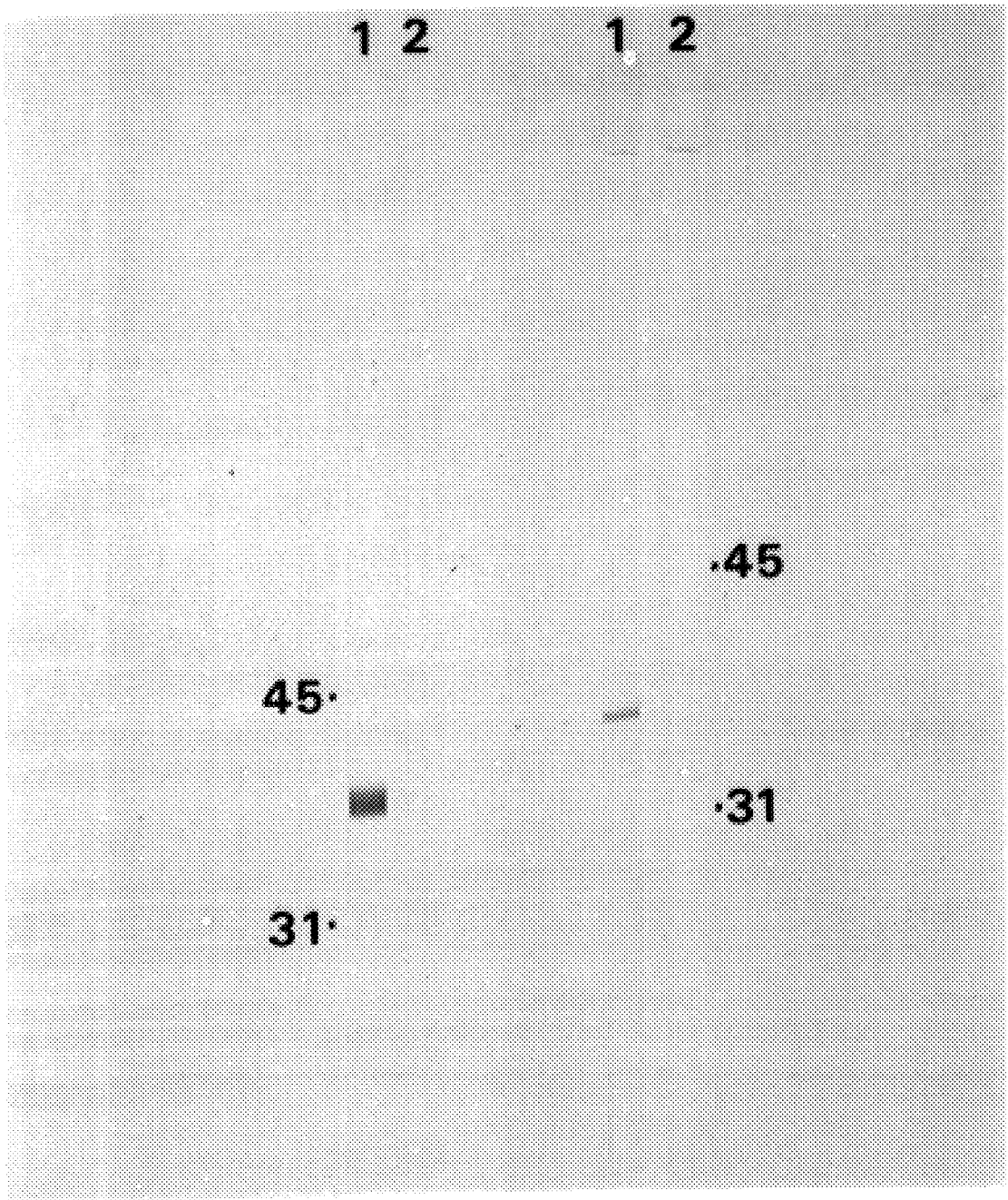
FIG. 1A–B shows a Western blot of *E. acervulina* (A) and *E. tenella* (B) sporozoite proteins probed with antiserum raised against Prep cell purified EASC2 protein (Lane 1) or pre-immmune control serum (Lane 2). Markers indicate molecular weight calibration in kD.

In general, the term "protein" refers to a molecular chain of amino acids with biological activity. A protein is not of a specific length and can, if required, be modified in vivo or in vitro, by, for example, glycosylation, amidation, carboxylation or phosphorylation; thus, inter alia, peptides, oligopeptides and polypeptides are included within the definition.

More part particularly, this invention provides proteins possessing LDH activity, or immunogenically active parts thereof, which have the amino acid sequence shown in SEQ ID NO. 2 and their biologically functional equivalents or variants.

The biologically functional equivalents or variants of the proteins specifically disclosed herein are proteins derived from the above-noted amino acid sequences, for example by deletions, insertions and/or substitutions of one or more amino acids, but retain one or more immunogenic determinants of the Eimeria antigens, i.e. said variants have one or more epitopes capable of eliciting an immune response in a host animal.

It will be understood that, for the particular proteins embraced herein, natural variations can exist between individual Eimeria parasites or strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science,227, 1435–1441, 1985) and determining the functional similarity between homologous proteins. Such amino acid substitutions of the exemplary embodiments of this invention are within the scope of the invention as long as the resulting proteins retain their immunoreactivity.

Furthermore, also immunogenic fragments of the proteins specifically disclosed herein or their functional variants are included in the present invention.

The term "fragment" as used herein means a DNA or amino acid sequence comprising a subsequence of the nucleic acid sequence or protein of the invention. Said fragment is or encodes a polypeptide having one or more immunogenic determinants of an Eimeria antigen. Methods for determining usable immunogenic polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Suitable immunogenic polypeptide fragments of a protein according to the invention containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on pepscan method, wherein a series of partially overlapping peptides corresponding with partial sequences of the complete polypeptide under consideration, are synthesized and their reactivity with antibodies is investigated.

In addition, a number of regions of the poly-peptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds, e.g. with the aid of Berzofsky's amphiphilicity criterion (Science 235, 1059–62, 1987).

The invention further provides isolated and purified nucleic acid sequences encoding the above mentioned proteins of Eimeria. One of these nucleic acid sequences is shown in SEQ/ID/NO: 1. It is well known in the art that the degeneracy of the genetic code permits substitution of bases in the codon resulting in another codon but still coding for the same amino acid, e.g. the codon for the amino acid glutamic acid is both GAT and GAA. Consequently, it is clear that, for the expression of a protein with the amino acid sequence shown in SEQ/ID/NO: 2, the nucleic acid sequence may have a codon composition different from the nucleic acid sequence shown in SEQ/ ID/NO: 1.

A nucleic acid sequence according to the present invention may be isolated from an Eimeria strain and multiplied by recombinant DNA techniques including polymerase chain reaction (PCR) technology or may be chemically synthesized in vitro by techniques known in the art.

A nucleic acid sequence according to the invention can be ligated to various replication effecting DNA sequences with which it is not associated, or linked in nature, resulting in a so-caled recombinant vector which can be used for the transformation of a suitable host. Useful recombinant vectors are preferably derived from plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids; bacteriophages, e.g. λgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol.,110, 1–24, 1990). The methods to be used for the construction of a recombinant vector according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restri ctio n enzyme(s) as co complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of an heterologous nucleic acid sequence into a host cell, irrespective of the method used, for example direct uptake or transduction. The heterologous nucleic acid sequence may be maintained through autonomous replication or, alternatively, may be integrated into the host genome. If desired, the recombinant vectors are provided with appropriate control sequences compatible with the designated host. These sequences can regulate the expression of the inserted nucleic acid sequence. In addition to microorganisms, cell cultures derived from multicellular organisms may also be used as hosts.

The recombinant vectors according to the invention preferably contain one or more marker activities that may be used to select for desired transformants, such as ampicillin and tetracycline resistance in pBR322, ampicillin resistance and α-peptide of β-galactosidase in pUC8.

A suitable host cell is a microorganism or cell which can be transformed by a nucleic acid sequence encoding a polypeptide or by a recombinant vector comprising such a nucleic acid sequence, and which can, if desired, be used to express said polypeptide encoded by said nucleic acid sequence. The host cell can be of prokaryotic origin, e.g. bacteria such as *Escherichia coli, Bacillus subtilis* and Pseudomonas species; or of eukaryotic origin such as yeasts, e.g. *Saccharomyces cerevisiae* or higher eukaryotic cells such as insect, plant or mammalian cells, including HeLa cells and Chinese hamster ovary (CHO) cells. Insect cells include the Sf9 cell line of *Spodoptera frugiperda* (Luckow et al., Biotechnology 6, 47–55, 1988). Information with respect to the cloning and expression of the nucleic acid sequence of the present invention in eukaryotic cloning systems can be found in Esser, K. et al. (Plasmids of Eukaryotes, Springer-Verlag, 1986).

In general, prokaryotes are preferred for the construction of the recombinant vectors useful in the present invention. *E. coli* K12 strains are particularly useful, especially DH5a or MC1061 strains.

For expression, nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector comprising a nucleic acid sequence encoding an Eimeria protein identified above operably linked to expression control sequences, which is capable of expressing the DNA sequences contained therein in (a) transformed host cell(s).

It should be understood, of course, that the nucleotide sequences inserted at the selected site of the cloning vector may include nucleotides which are not part of the actual structural gene for the desired polypeptide, or may include only a fragment of the complete structural gene for the desired protein as long as the transformed host will produce a polypeptide having at least one or more immunogenic determinants of an Eimeria protein antigen.

When the host cells are bacteria, useful expression control sequences which may be used include the Trp promotor and operator (Goeddel, et al., Nucl. Acids Res., 8, 4057, 1980); the lac promotor and operator (Chang, et al., Nature, 275, 615, 1978); the outer membrane protein promotor (Nakamura, K. and Inouge, M., EMBO J., 1, 771–775, 1982); the bacteriophage lambda promotors and operators (Remaut, E. et al., Nucl. Acids Res., 11, 4677–4688, 1983); the (α-amylase (*B. subtilis*) promotor and operator, termination sequences and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include the SV-40 promotor (Berman, P. W. et al., Science, 222, 524–527, 1983) or the metallothionein promotor (Brinster, R. L., Nature, 296, 39–42, 1982) or a heat shock promotor (Voellmy et al., Proc. Natl. Acad. Sci. USA, 82, 4949–53, 1985). Alternatively, expression control sequences present in Eimeria may also be applied. For maximizing gene expression, see also Roberts and Lauer (Methods in Enzymology, 68, 473, 1979).

Therefore, the invention also comprises (a) host cell(s) containing a nucleic acid sequence or a recombinant nucleic acid molecule or a recombinant vector described above, capable of producing the Eimeria protein by expression of the nucleic acid sequence.

Immunization of poultry against Eimeria infection can be achieved by administering to the birds a protein according to the invention in an immunologically relevant context as a subunit vaccine. The subunit vaccine according to the invention may comprise a protein in a pure form, optionally in the presence of a pharmaceutically acceptable carrier. The protein can optionally be covalently bonded to a non-related protein, which can be of advantage in the purification of the fusion product. Examples are β-galactosidase, protein A, prochymosine, blood clotting factor Xa, etc.

In some cases the ability to raise protective immunity using these proteins per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelles of anphiphilic compounds like saponins. Alternatively these fragments may be provided as polymers thereof, preferably linear polymers.

If required, the proteins according to the invention which are to be used in a vaccine can be modified in vitro or in vivo, for example by glycosylation, acylation, amidation, carboxylation or phosphorylation.

A newly developed vaccine version is a vaccine in which the DNA coding for the protein of the invention is administered in a pharmaceutically acceptable form, for instance in the form of "bullets", which can be shot into the tissue. This naked DNA can be used as vaccine provided it is presented in a plasmid or in combination with suitable eukaryotic promoter sequences such as those from SV40 virus. In this way one can achieve the introduction of this DNA into the genomic DNA, thus ensuring the expression of the antigen in situ.

An alternative to subunit vaccines is live vaccines. A nucleic acid sequence according to the invention is introduced by recombinant DNA techniques into a microorganism (e.g. a bacterium or virus) in such a way that the recombinant microorganism is still able to replicate, thereby expressing a polypeptide coded by the inserted nucleic acid sequence and eliciting an immune response in the infected host bird.

A preferred embodiment of the present invention is a recombinant vector virus comprising an heterologous nucleic acid sequence described above, capable of expressing the DNA sequence in (a) host cell(s) or host bird infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the Eimeria protein by expression of the nucleic acid sequence.

For example the well known technique of in vivo homologous recombination can be used to introduce an heterologous nucleic acid sequence according to the invention into the genome of the vector virus.

First, a DNA fragment corresponding with an insertion region of the vector genome, i.e. a region which can be used for the incorporation of an heterologous sequence without disrupting essential functions of the vector such as those necessary for infection or replication, is inserted into a cloning vector according to standard recDNA techniques. Insertion-regions have been reported for a large number of microorganisms (e.g. EP 80,806, EP 110,385, EP 83,286, EP 314,569, WO 88/02022, WO 88/07088, U.S. Pat. No. 4,769, 330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion region present in the recombinant vector of the first step or in place of the DNA deleted from said recombinant vector. The insertion region DNA sequence should be of appropriate length as to allow homologous recombination with the vector genome to occur. Thereafter, suitable cells can be infected with wild-type vector virus or transformed with vector genomic DNA in the presence of the recombinant vector containing the insertion flanked by appropriate vector DNA sequences whereby recombination occurs between the corresponding regions in the recombinant vector and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant microorganism can be administered to poultry for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769, 330 and U.S. Pat. No. 4,722 848) or fowl pox virus (WO 88/02022), herpes viruses such as HVT (WO 88/07088) or Marek's Disease virus, adenovirus or influenza virus, or bacteria such as E. coli or specific Salmonella species. With recombinant microorganisms of this type, the polypeptide synthesized in the host animal can be exposed as a surface antigen. In this context fusion of the polypeptide with OMP proteins, or pilus proteins of for example E. coli or synthetic provision of signal and anchor sequences which are recognized by the organism are conceivable. It is also possible that the Eimeria polypeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector comprising a nucleic acid sequence according to the invention, whereafter recombinant bacteria or vector containing cells and/or recombinant vector viruses grown in the cells can be collected, optionally in a pure form, and formed into a vaccine optionally in a lyophilised form.

Host cells transformed with a recombinant vector according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed into a vaccine, depending on its intended use. In order to purify the polypeptides produced, host cells transformed with a recombinant vector according to the invention are cultured in an adequate volume and the polypeptides produced are isolated from such cells, or from the medium if the protein is excreted. Polypeptides excreted into the medium can be isolated and purified by standard techniques, e.g. salt fractionation, centrifugation, ultrafiltration, chromatography, gel filtration or immunoaffinity chromatography, whereas intracellular polypeptides can be isolated by first collecting said cells, disrupting the cells, for example by sonication or by other mechanically disruptive means such as French press, followed by separation of the polypeptides from the other intracellular components and forming the polypeptides into a vaccine. Cell disruption could also be achieved by chemical (e.g. EDTA or detergents such as Triton X114) or enzymatic means, such as lysozyme digestion.

Antibodies or antiserum directed against a polypeptide according to the invention have a potential use in passive immunotherapy, diagnostic immunoassays and generation of anti-idiotypic antibodies.

The Eimeria proteins as characterized above can be used to produce antibodies, both polyclonal, monospecific and monoclonal. If polyclonal antibodies are desired, techniques for producing and processing polyclonal sera are known in the art (e.g. Mayer and Walter. eds, Immunochemical Methods in Cell and Molecular Biology, Academic Press, London,1987). Monospecific antibodies to an immunogen can be affinity purified from polyspecific antisera by a modification of the method of Hall et al. (Nature, 311, 379–387, 1984). Monospecific antibody, as used herein, is defined as a single antibody species or multiple antibody species with homogeneous binding characteristics for the relevant antigen. Homogeneous binding, as used herein, refers to the ability of the antibody species to bind to a specific antigen or epitope.

Monoclonal antibodies, reactive against the Eimeria proteins according to the present invention, can be prepared by immunizing inbred mice by techniques known in the art (Köhler and Milstein, Nature, 256, 495–497, 1975). Hybridoma cells are selected by growth in hypoxanthine, thymidine and aminopterin in an appropriate cell culture medium such as Dulbecco's modified Eagle's medium. Antibody producing hybridomas are cloned, preferably using the soft agar technique of MacPherson, (Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotypic antibodies are immunoglobulins which carry an "internal image" of the antigen of the pathogen against which protection is desired and can be used as an immunogen in a vaccine (Dreesman et al., J. Infect. Disease, 151, 761, 1985). Techniques for raising anti-idiotypic antibodies are known in the art (MacNamara et al., Science, 226, 1325, 1984).

The vaccine according to the invention can be administered in a conventional active immunization scheme: single or repeated administration in a manner compatible with the dosage formulation, and in such amount as will be prophylactically effective, i.e. the amount of immunizing antigen or recombinant microorganism capable of expressing said antigen that will induce immunity in poultry against challenge by virulent Eimeria parasites. Immunity is defined as the induction of a significant level of protection in a population of chickens after vaccination compared to an unvaccinated group.

Next to an increase in protection a vaccine comprising the polypeptide of the invention will also reduce the number of oocysts shedded by the infected animals. Normally, the shedded oocysts will infect other animals in the flock. A decrease in the number of oocysts shedded will then also give a decrease in the number of animals which is subsequently infected and also a decrease in the number of oocysts shedded will give rise to a lesser infective load.

Furthermore, even without effect on the parasite itself, a vaccine can decrease the incidence of disease. This is especially so when the symptoms of the disease are caused by products released by the parasite. Vaccines directed against such products alleviate the symptoms without attacking the parasite.

For live viral vector vaccines the dose rate per chicken may range from $10^5$–$10^8$ pfu. A typical subunit vaccine according to the invention comprises 1 μg–1 mg of the protein according to the invention. Such vaccines can be administered intradermally, subcutaneously, intramuscularly, intraperitoneally, intravenously, orally or intranasally.

Additionally the vaccine may also contain an aqueous medium or a water containing suspension, often mixed with other constituents in order to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

A vaccine comprising the polypeptide of the invention may also comprise other immunogenic proteins of *E. maxima* or immunogenic proteins of other Eimeria species. Such a combination vaccine will decrease the parasitic load in a flock of poultry and will increase the level of protection against coccidiosis.

It is clear that a vaccine according to the invention may also contain immunogens related to other pathogens of poultry, or may contain nucleic acid sequences encoding these immunogens, like antigens of Marek's Disease virus (MDV), Newcastle Disease virus (NDV), Infectious Bronchitis virus (IBV), Chicken Anemia Agent (CAA), Reovirus, Avian Retrovirus, Fowl Adenovirus, Turkey Rhinotracheitis virus or *E. coli* to produce a multivalent vaccine.

The invention is illustrated by the following examples:

EXAMPLE 1

Handling of Parasites

*Eimeria acervulina* (Houghton strain) and *Eimeria tenella* (Weybridge strain) parasites were collected after deliberate infection of chickens reared in the absence of coccidia. *E. acervulina* oocysts were isolated from fecal material on days 4 and 5 post-infection (p.i.). *E. tenella* oocysts were harvested from the ceca on day 7 p.i.

The oocysts were sporulated with strong aeration at 30° C. for 7 hours, resulting in partially sporulated oocysts. Release of sporocysts and sporozoites of 48 hr sporulated oocysts was performed as described earlier in A. N. Vermeulen et al. FEMS Microbiological Letters 110, (1993), 223–230.

To obtain *E. acervulina* intracellular stages, chickens were infected at 5 weeks with $10^8$ sporulated *E. acervulina* oocysts. Intracellular parasites were harvested from the duodenum after 42 hours. Hereto chickens were exsanguinated 42hr post inoculation and duodenum was removed from the stomach to Meckel's diverticulum. The tissue was washed and cut into small pieces of approximately 1 cm$^3$. The pieces were suspended in calcium/magnesium free Hanks BSS containing 10 mg/ml glucose (CMF-Hanks). Epithelial cells were released from the matrix by 10 min incubation in EDTA (2 mM EDTA in CMF Hanks at 35–37° C.). Supernatants of four incubations were pooled and centrifuged 10 min at 750 g, which pelleted the cells. The intracellular parasites (further called "schizonts", although also trophozoites were present) were subsequently released from the host cells by saponin lysis (15 min in 0.1% saponin in CMF-Hanks at roomtemperature) and mechanical shearing.

The schizonts were pelleted and separated from host material after centrifugation through 45% Percoll (Pharmacia Fine Chemicals) (20 min, 700 g, 4° C.). Dry pellets of schizonts were stored at −70° C. until further use.

Triton X114 Extraction

Triton X114 extractions were carried out to obtain the hydrophilic protein fraction of schizonts. The procedure used was described earlier by C. Bordier (1981) Journal of Biological Chemistry, vol. 256 no. 4 (feb) pp. 1604–1607.

$10^8$ to $10^9$ *E acervulina* schizonts per ml of TBS (10 mM Tris-HCl, 150 mM NaCl pH7.4) were sonified±3×20 sec. on ice with the microtip (Branson sonifier, position 7). PMSF (final concentration 1 mM) and DNase/RNase (final concentration for both 0.02 mg/ml) was added (DNase/RNase stock: 2 mg/ml DNase, 2 mg/ml RNase in 5 mM MgCl2).

Precondensed Triton X114 was added to the sonified schizonts in suspension to a final concentration of 10% (v/v) and mixed well to dissolve the proteins. The non-extractable material was pelleted by centrifugation 20 min 12,000 g at 4° C. The soluble fraction was layered over a sucrose cushion (6% sucrose, 0.06% (v/v) TX114 in TBS), incubated 10 min 40° C. and spun 10 min 400 g at room temperature. The hydrophilic fraction was extracted again by the same procedure.

The hydrophilic fractions were stored at −70° C. until further use. Total protein concentration was determined using the BCA (Pierce Chemicals) assay.

Prep-Cell Fractionation

Hydrophilic proteins were further separated with respect to their relative molecular mass on SDS-PAGE under reducing conditions in the Laemmli buffer system. Hereto we made use of preparative electrophoresis in the so-called Prepcell.

Materials:
Prepcell apparatus (Biorad Labs) with Prepcell column (37mm ID)
Dialysis membrane for Prep cell (cut off 6 kD)
Power supply (EPS 600 Pharmacia)
Reducing sample buffer: 62.5 mM Tris-HCl pH 6.8; 10% glycerol; 2% SDS; 0.01% bromophenol blue (Merck); 0.13 M DTT (dithiothreitol, Merck)
Electrophoresis buffer/elution buffer: 25 mM Tris, 192 mM Glycine, 0.1% SDS pH8.6
Method and Results:

All procedures were performed at 4° C. For the fractionation of the hydrophilic proteins a 4% stacking/9% separating gel (polyacrylamide) was used in the 37 mm tube (filled to 6 cm) of the Prepcell according to the manufacturers protocol, but with the addition of 0.1% SDS.

The hydrophilic phase of TX114 extractions kept at −70° C. was thawed and the hydrophilic proteins (about 8 mg per run) were diluted in reducing sample buffer (total volume was ±6 ml), boiled 3 min 100° C., and were loaded on the surface of the 4% stacking gel using a narrow tube affixed to a syringe.

The Prepcell was connected to the power supply and electrophoresis was started at 40 mA, 500V max.

The collection of fractions (fraction volume ±2.5–3ml; flow 0.6 ml/min) started after about 6 hours, when the tracking dye eluted from the cell. Fractions were collected overnight (±100 fractions) in plastic 3.5 ml tubes (Sarstedt).

Samples of the fractions were taken for analysis by SDS-PAGE and Western blotting. Fractions were stored at −70° C.

This purification method resulted in fractions containing almost pure proteins as follows from analyses shown below.

Amino Acid Sequencing

Selected fractions of Prepcell run COC9314612 containing an almost pure band around Mr=37 k (designated as EASC2) were pooled, concentrated by acetone precipitation and run on a 12% PAAgel. The gel was shortly stained with a non-denaturing Coomassie Brilliant Blue staining protocol: staining: 20 min at ambient temperature in 0.2% CBB in 20% methanol/0.5% acetic acid. Destaining: 60 min in 30% methanol.

The staining 37 kD band was cut out. Internal amino acid sequencing was performed on a selected HPLC-purified peptide of a trypsin digest of the EASC2, all performed by Eurosequence BV Groningen The Netherlands.

The amino/acid sequence of the tryptic peptide was GWIKQEEVDDIVQK (see SEQ.ID.No: 2 amino acids 212–225).

This coding sequence for this peptide was also detected after DNA sequencing of the clone.

EXAMPLE 2

Preparation of Monospecific Antibodies in Rabbits

Prevaccination sera of SPF rabbits were screened on Western blotted *E. acervulina* antigens of different developmental stages and on a blot of *E coli* proteins. 'Negative' rabbits were selected for the raising of antibodies.

Fractions of Prepcell runs containing EASC2 (37 kD) were selected by $S^6S$-PAGE, pooled and concentrated (±3×) with an Amiconcell (YM10 filter) to 3.5 ml.

The rabbit was twice immunized with concentrated antigen in GNE (8×0.25 ml i.c.; 1 ml i.p.) with an interval of 4 weeks. Two weeks after the second immunisation the rabbit was bled and sera were tested on Western blots of *Eimeria acervulina* en tenella sporozoites and schizonts 42 hr. FIG. 1 shows the result of the immunodetection of the monospecific antiserum on sporozoite antigens of both species. It appeared that the antibodies recognised a parasite product of about 37 kD in both *E. acervulina* (Lane A1) and *E. tenella* (Lane B1). Control sera of the same rabbit prior to immunization did not recognise these bands (Lanes A/B2). The protein is also present in schizont stages of the two species (not shown).

EXAMPLE 3

Vaccination of Chickens with *E.acervulina* TX114 Hydrophilic Fraction and EASC2

The TX114 hydrophilic phase of schizont material was separated and dialysed extensively against 0.01M PBS pH 7.3 at 4° C.

Selected fractions containing the EASC2 37 kD protein were dialysed extensively against 3×5 liter 0.01 M PBS pH 7.3 at 4° C.

The concentration of protein in the vaccine preparations was estimated by staining different concentrations of sample with CBB after SDS-PAGE and comparing the intensity of the staining with a reference sample of BSA.

The volumes were corrected to obtain ±5 µg protein/dose for the purified protein and about 15 µg/dose for the total hydrophilic fraction.

These were stored as aliquotted volumes for priming and booster vaccination at −70° C. Frozen vaccine preparations were thawed.

To every 15 ml of vaccine 3.2 mg Quil A Superfos Biosector was added as adjuvant in a volume of 1 ml 0.01 M PBS pH 7.3.

Vaccine was mixed well by vortexing and injected in 4–6 week old coccidia-free White Leghorn chickens in 0.75 ml given subcutaneously.

The vaccine contained 150 µg Quil A/dose.

Figure 2:
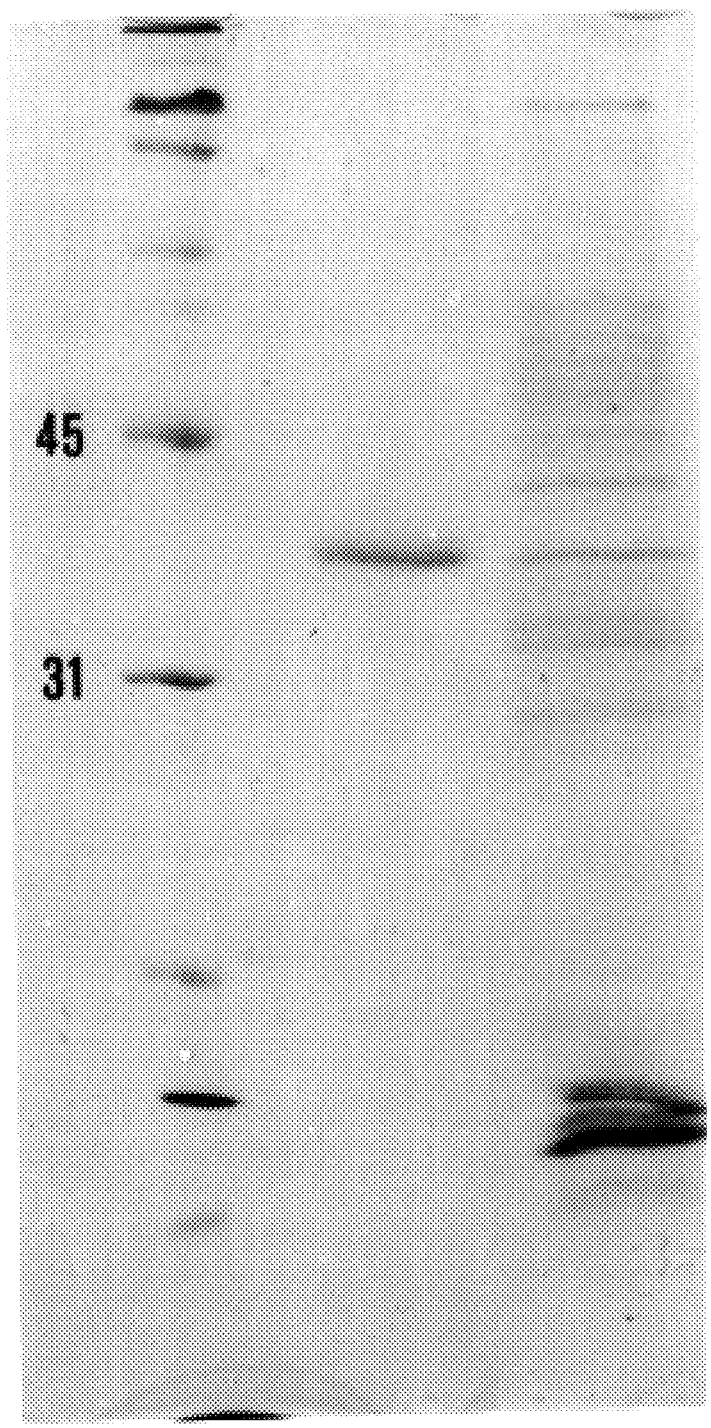
FIG. 2 shows Coomassie Brilliant Blue stained SDS-PAGE of Prep cell purified EASC2 protein (Lane 1) or TX114 hydrophilic fraction of *E. acervulina* 42 hr schizonts (lane 2). Lane M contains molecular weight calibration marker in kD.

FIG. 2 shows a Coomassie BB stained SDS-PAGE of the EASC2 (Lane 1) and 42 hr TX114 hydrophilic fraction (Lane 2) injected into the chickens as vaccine.

Four weeks after priming birds were boosted with the same dose via the same route. The booster vaccine was prepared freshly from the frozen antigen stock.

Control chickens were inoculated with 150 µg Quil A/dose in PBS. Each group comprised 14 chickens.

Eleven days after the boosting vaccination all chickens were inoculated orally with 240 sporulated oocysts of *Eimeria acervulina* H in 1 ml of 15% sucrose in water.

Chickens were placed in cages 2 birds per cage. Oocyst output was assessed in fecal samples taken from days 4 to 8 after challenge.

Table 2 shows the results of this experiment. Oocyst output is expressed as % oocysts from the output in the control animals.

Statistical evaluation of the data was performed on the LOG of the number of oocysts using Student's T-test or Mann-Whitney's test if data distribution was not normal.

When p<<0.05 the difference was regarded significant.

This table shows that both the TX114 fraction and the EASC2 prepcell purified fraction induce a statistically significant reduction (p<0.05) in oocyst output after challenge.

Prepcell purification seemed to improve the protection induced by the TX114 vaccine.

TABLE 2

| Immunogen | Oocyst output in percents from control and statistical value of difference | |
|---|---|---|
| | % oocyst output from control ± S.D. | p value different from control |
| EASC2 prep cell pure ± 5 µg/dose | 72 ± 30 | p = 0.01 |
| Hydrophilic TX114 proteins of Schizonts ± 15 µg/dose | 84 ± 17 | p = 0.02 |

In another experiment in which only total extracts of 42 hr schizonts were used as vaccine no significant oocyst reduction could be induced (results not shown).

In a second experiment Prepcell purified EASC2 was used in two different concentrations of 0.2 and 2 µg/dose. Following the same protocol for immunization and challenge, protection was measured in ten chickens per group as reduction of oocyst output compared to the group inoculated with PBS/QuilA.

Table 3 summarises the average percentual oocyst output of the control for the two EASC2 vaccinated groups. This table demonstrates that the EASC2 protected in a dose dependent manner showing a statistically significant difference at a dose of 2 µg/dose.

TABLE 3

Oocyst output in percents from control and
statistical value of difference

| Group | % oocysts ± S.D. (control output = 100%) | significance of difference from control (p-value) |
|---|---|---|
| EASC2/Quil A 2 µg/dose | 64.0 ± 22 | 0.008 |
| EASC2/Quil A 0.2 µg/dose | 90.2 ± 27 | NOT SIGNIFICANT |

EXAMPLE 4

Immunological Stimulation After Vaccination with EASC2 or TX114 Hydrophilic Proteins.

In both protection experiments mentioned above chickens were assayed for stimulation of immunological parameters such as T-lymphocyte proliferation and serum antibodies.

Serum antibodies

Antibodies recognising the vaccine constituents were only detected in sera from the groups vaccinated with the 42 hr TX114-hydrophilic fraction and not the group vaccinated with the purified EASC2.

Lymphocyte proliferation

Lymphocyte proliferation after antigenic stimulus was tested in a lymphocyte stimulation test (LST).

Method:

Prior to challenge peripheral blood cells were taken from all chickens of each group.

Peripheral blood leucocytes (PBL) were isolated by centrifugation 3 ml of the total blood for 7 min at 64 g at ambient temperature. The buffy coat was collected in RPMI 1640 (Dutch modification) and washed two times. Cell concentration was adjusted to $1 \times 10^7$ cells per ml in RPMI 1640. The RPMI 1640 (Dutch modification) used was supplemented with sodium pyruvate (1 mM), Glutamine (2 mM), penicillin 200 U/ml and streptomycin 200 µg/ml.

96 well round-bottom tissue culture plates were seeded with 0.05 ml cell suspension with 3.0% chicken serum (Gibco BRL), 0.05 ml "stimulating antigen" suspension and 0.05 ml RPMI 1640, cultured for 64 hr at 41° C. under 5% $CO_2$ atmosphere. Subsequently 18.5 kBq 3-H-Thymidine (Amersham Beckenham U.K.) was added per well and 8 hrs later the cells were harvested on a glass-fibre filter (Skatron Norway Bluemat) using a 96 well Cell Harvester (Skatron Norway). The filters were saturated with scintillation fluid (LKB BetaScint) and counted in a Betaplate 1205 (Pharmacia / LKB Sweden).

As "stimulating antigen" E.acervulina schizonts were used, which were sonicated using a microtip-equipped Branson sonifier at position 6 for 3×20 seconds with intermediate cooling and stored at −70° C. The antigens were thawed before use and diluted to meet the concentration used for the stimulation. PBL of all groups were stimulated with $3.10^5$ E. acervulina schizonts.

Statistical evaluation was performed using Student's T-test on the LOG of the Stimulation Index (SI) (the number of counts per min (cpm) of the stimulated cultures divided by the cpm of the non-stimulated control). When p<0.05 the difference was regarded significant.

Results:

Table 4. shows the mean S.I. for the groups from both experiments described above. The first experiment in which EASC2 vaccine was compared with the TX114-hydrophilic fraction, and the second experiment dealing with the two dosages of the EASC2 vaccine.

It appeared that all antigens or dosages induced a significant positive T-cell response detectable in the peripheral blood at the time of challenge.

In both experiments, however, the higher dose of the Prepcell pure EASC2 vaccine (2 or 5 µg/dose) induced the very highest stimulation of T-cells. The ranking of the T-cell stimulation correlated with the reduction in oocyst output after challenge.

Table 4. Mean incorporation of $^3$H-Thymidine after stimulation with E. acervulina schizonts by PBL from groups immunised with the different vaccines, expressed as Stimulation Index (S.I)±Standard Error (SE).

| Experiment | Group | $^3$H-thymidine incorporation in S.I. ± SE |
|---|---|---|
| I | EASC2 5 µg | 120 ± 47 @ |
|  | TX114 hydrophilic proteins | 31 ± 12 @ |
|  | Placebo | 6 ± 1 |
| II | EASC2 2 µg | 112 ± 28 @ |
|  | EASC2 0.2 µg | 24 ± 4 @ |
|  | Placebo | 2.3 ± 0.3 |

@) Significant from control group p < 0.001

EXAMPLE 5

Cloning Experiments

Sporulation of E. acervulina oocysts

A suspension of $5*10^8$ E. acervulina oocysts in 60 ml $10^{-4}$M sodium dithionite was centrifuged, after which the pellet was washed once with 100 ml sterile water. The cells were resuspended in 500 ml 2% potassium bichromate and then incubated under the influence of strong aeration for 7 hours at 30° C. The oocysts were then collected by centrifuging and washed three times with 200 ml sterile water.

Isolation of RNA

For the isolation of RNA (Pasternak J. et al., Mol. & Bioch. Par. 3, 133–142, 1981) the cell pellet was taken up into 2.8 ml of buffer containing 10 mM Tris acetate (pH7.6), 75 mM sodium acetate, 1% SDS, 2 mM EDTA, 0.2 mg/ml proteinase K and 10 mM vanadyl ribonucleoside complexes. The oocysts were destroyed by vortexing for 60 seconds (max) in the presence of 13 g glass beads (ø0.5 mm). 5 ml of phenol was added to the total extract and the mixture was vortexed for a further 60 seconds. After centrifuging, the supernatant liquor was pipetted off and again extracted with an equal volume of phenol/chloroform/isoamyl alcohol (25:24:1). RNA was precipitated after adding 2.5 volume ethanol and the resulting precipitate was dissolved in 800 ml Tris 10 mM, EDTA 0.1 mM pH 7.6 ($T_{10}E_{0.1}$), after which the product was extracted a further twice with an equal volume of phenol/chloroform/isoamyl alcohol (25:24:1) and twice with chloroform/isoamyl alcohol (24:1) and then precipitated with ethanol. PolyA$^+$-RNA was isolated by means of oligo(dT)-cellulose chromatography (Maniatis T. et al.: Molecular Cloning. Cold Spring Harbor Laboratory, 1982). Approximately 100 µg polyA$^+$-RNA was isolated from $5*10^8$ oocysts.

cDNA synthesis

PolyA$^+$-RNA was converted to cDNA by means of the enzyme MMLV reverse transcriptase. For this purpose 25 µg polyA+-RNA was dissolved in 90 ml of water and denatured for 5 minutes at 20° C. by adding mercury methyl hydroxide to 10 mM, after which β-Mercaptoethanol was added to 45 mM and the mixture incubated for a further 3 minutes at 20° C. The enzyme reaction was carried out in 190 ml buffer containing 4 mg oligo(dT)15, 150 U RNasin(R), 20 mM Tris (pH 7.6), 30 mM KCl, 4 mM dithiothreitol (DTT), 2 mM MgCl$_2$, 1 mM of each dNTP and 3000 U MMLV reverse transcriptase. The reaction was stopped after 1 hour incubation at 37° C. by adding 10 ml 0.5 M EDTA. After extraction with an equal volume of phenol/chloroform/isoamyl alcohol (25:24:1), the RNA/DNA hybrid was precipitated by adding ammonium acetate to 2 M and 2.5 volumes ethanol. The combined action of the enzymes DNA-polymerase I and RNase H (Gubbler U. et al., Gene 25, 263–269, 1983) results in the synthesis of the second string. The pellet was dissolved in 960 μl of buffer containing 20 mM Tris (pH 7.6), 5 mM MgCl$_2$, 100 mM (NH$_4$)$_2$SO$_4$, 0.6 mM β-NAD, 16 U RNase H, 200 U DNA-polymeraseI and 20 U DNA-ligase (*E.coli*). The incubation time was 1 hour at 12° C. and then 1 hour at 22° C., after which the reaction was stopped by adding an equal volume of phenol/chloroform/isoamyl alcohol (25:24:1) and precipitating with ethanol.

Before the cDNA was cloned in a vector suitable for this purpose it was first modified. cDNA (5 μg) was dissolved in 100 μl of buffer containing 30 mM sodium acetate (pH 5.6), 50 mM NaCl, 1 mM ZnSO$_4$ and 21 U Mung Bean Nuclease. After incubation for 30 minutes at 37° C. the reaction was stopped by adding EDTA to 10 mM and Tris to 25 mM. After extraction with phenol/chloroform/isoamylalcohol (25:24:1) the mixture was desalinated over a Sephadex G50 column. The following were added to the eluate (125 μl): Tris pH 7.6 to 50 mM, EDTA to 2.5 mM, DTT to 5 mM, S'-adenosylmethionine to 0.5 mM and 100 U EcoRI-methylase. After incubation for 30 minutes at 37° C., the reaction was stopped by heating for 15 minutes at 65° C., after which 1/10 volume of a solution containing Tris-HCl 100 mM, MgCl$_2$ 100 mM and NaCl 500 mM (pH7.5) was added, and, at the same time, each dNTP to 1 mM and 12.5 U Klenow DNA-polymerase. The reaction was stopped by adding an equal volume of phenol/chloroform/isoamyl alcohol (25:24:1) after incubating for 60 minutes at 22° C. The supernatant liquor was precipitated after adding 350 μl H$_2$O and 50 μl 3 M sodium acetate (pH 5.6) with 500 μl isopropanol. After dissolving in 100 ml H$_2$O, the pellet was desalinated over Sephadex G50 and the eluate precipitated with ethanol. After dissolving the pellet in 24 μl H$_2$O, ligation was carried out in 50 μl by adding 2 μg EcoRI linker, Tris-HCl(pH 8.0) to 30 mM, MgCl$_2$ to 10 mM, dithiothreitol to 10 mM, ATP to 1 mM, gelatin to 0.1 mg/ml and 10 U T4DNA-ligase. The reaction was stopped after 16 hours incubation at 4° C. by heating (for 15 minutes at 70° C.) after which cutting was carried out with restriction endonuclease EcoRI in 210 μl buffer containing 100 mM Tris-HCl (pH 7.6), 50 mM NaCl, 10 mM MgCl$_2$, 2.5 mM DTT and 500 U EcoRI. After 90 minutes incubation at 37° C., the reaction was stopped by means of extraction with an equal volume of phenol/chloroform/isoamylalcohol (25:24:1). The supernatant liquor was precipitated with 2.5 volume ethanol after adding sodium acetate (pH 5.6) to 300 mM cDNA and linkers were separated by means of a Biogel A15M column. The cDNA was precipitated with ethanol, after which the precipitate was dissolved in Tris-HCl 10 mM, EDTA 0.1 mM(pH 7.6). The cDNA molecules were then cloned in phage lambda ZAPII (Stratagene).

Screening of the cDNA bank ($2*10^5$ pfu) with antibodies directed against the EASC2 protein fraction of *E acervulina* schizonts revealed six positive phage clones. These antibodies were deluted 1:2000 with 1×Tris salt (Tris-HCl 10 mM, NaCl 150 mM, pH 8.0)+0.05% Tween 20+10% Foetal Calf Serum (FCS) and incubated for two hours at room temperature(RT) with the filters. The filters were then washed 4 times, for 10 minutes each time, with 50 ml 1×Tris salt+0.05% Tween 20, each filter. For the second antibody incubation a conjugate of goat-anti-rabbit antibodies and alkaline phosphatase was used (diluted 1:7500 in 1×Tris salt+0.05% Tween 20+10% FCS) and incubated for 30 minutes at RT, after which the filters were washed as described after the first antibody incubation. The colour reaction was carried out in Tris-HCl 100 mM, NaCl 100 mM, MgCl$_2$ 10 mM, (pH 9.6), in which 0.33 mg/ml Nitrobluetetrazolium and 0.17 mg/ml 5-bromo-4-chloro-3-indolyl phosphate were dissolved. The filters were evaluated after 30 minutes incubation at RT. The immunopositive clones were plaque-purified and rescued by means of in vivo excision, according to the protocol of the manufacturer (Stratagene). Plasmid DNA was isolated, from the resulting in vivo excision clones, for sequencing purposes according to standard protocols (Maniatis T., et al. supra). Partial sequence information showed all clones to be homologous, from the largest clone the nucleotide sequence was determined completely. This clone, designated pBLUE EASC2, contained an insert of 1566 bp.

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1679 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
  (A) ORGANISM: Eimeria acervulina
  (D) DEVELOPMENTAL STAGE: Schizont (vii) IMMEDIATE SOURCE:
  (B) CLONE: EASC2_1

(ix) FEATURE:
  (A) NAME/KEY: CDS
  (B) LOCATION:280..1269
  (D) OTHER INFORMATION:/function= "Eimeria lactate dehydrogenase"

(ix) FEATURE:
  (A) NAME/KEY: misc_feature
  (B) LOCATION:1..51
  (D) OTHER INFORMATION:/label= pBluescriptII (ix) FEATURE:
  (A) NAME/KEY: misc_feature
  (B) LOCATION:1624..1679
  (D) OTHER INFORMATION:/label= pBluescriptII (ix) FEATURE:
  (A) NAME/KEY: misc_feature
  (B) LOCATION:45..54
  (D) OTHER INFORMATION:/label= EcoRI-linker (ix) FEATURE:
  (A) NAME/KEY: misc_feature
  (B) LOCATION:1621..1630
  (D) OTHER INFORMATION:/label= EcoRI-linker (xi) SEQUENCE DESCRIPTION: SEQ ID NO: 1:

```
GCGGTGGCGG CCGCTCTAGA ACTAGTGGAT CCCCCGGGCT GCAGGAATTC GGGTTTTTTT      60

TTTTTTTTCT ACACATTAAT ATTCTTCGTT TACGTTTATT TTGCTACAAA TAAACCCCTT     120

AAACTCTCTA TTTCCTCATA TTCTACCGCT TCATCGGTGG GTGTGTAAGA CGTACGTACG     180

TACAGCTGGG GCTGGCTTAC TGCGCACCGC TTATTTATTA CTTAATTCAT ACACATTTTA     240

TATCTTTCTT CTTCTTTTTT CTTGCTCTTT CTTGTGAAA ATG GCG GTC TTC GAG        294
                                             Met Ala Val Phe Glu
                                               1               5

AAG AAT ACA CGC CCC AAG ATT GCT ATG GTG GGC TCC GGT ATG ATT GGA      342
Lys Asn Thr Arg Pro Lys Ile Ala Met Val Gly Ser Gly Met Ile Gly
             10                  15                  20

GGC ACC ATG GCT TTC CTG TGC AGC TTG AGG GAA CTC GGA GAT GTT GTC      390
Gly Thr Met Ala Phe Leu Cys Ser Leu Arg Glu Leu Gly Asp Val Val
         25                  30                  35

CTC TTC GAC GTT GTA CCG AAC ATG CCG ATG GGG AAG GCG ATG GAT ATA      438
Leu Phe Asp Val Val Pro Asn Met Pro Met Gly Lys Ala Met Asp Ile
     40                  45                  50

TCG CAC AAT TCG TCG GTG GTT GAC ACG GGT ATA ACA GTA TAC GGC TCA      486
Ser His Asn Ser Ser Val Val Asp Thr Gly Ile Thr Val Tyr Gly Ser
 55                  60                  65

AAT TCA TAC GAG TGC TTG AAG GGT GCG GAC GTA GTA ATA ATA ACA GCA      534
Asn Ser Tyr Glu Cys Leu Lys Gly Ala Asp Val Val Ile Ile Thr Ala
 70                  75                  80                  85

GGG ATA ACA AAG ATA CCC GGA AAG AGC GAT AAA GAA TGG TCT AGA ATG      582
Gly Ile Thr Lys Ile Pro Gly Lys Ser Asp Lys Glu Trp Ser Arg Met
                 90                  95                 100

GAT CTA TTA CCT GTG AAT ATA AAG ATA ATG AGG GAG GTC GGT GCA GCA      630
Asp Leu Leu Pro Val Asn Ile Lys Ile Met Arg Glu Val Gly Ala Ala
             105                 110                 115

ATT AAA TCT TAC TGT CCT AAT GCA TTT GTT ATT AAT ATA ACA AAT CCT      678
```

```
Ile Lys Ser Tyr Cys Pro Asn Ala Phe Val Ile Asn Ile Thr Asn Pro
        120                 125                 130

TTA GAT GTG ATG GTA GCT GCT CTT CAA GAG TCA TCA GGA CTA CCT CAT      726
Leu Asp Val Met Val Ala Ala Leu Gln Glu Ser Ser Gly Leu Pro His
    135                 140                 145

CAT AGA ATC TGC GGT ATG GCT GGG ATG CTT GAT AGC TCT CGT TTT AGA      774
His Arg Ile Cys Gly Met Ala Gly Met Leu Asp Ser Ser Arg Phe Arg
150                 155                 160                 165

CGT ATG ATA GCT GAT AAA TTA GAA GTC TCT CCT AGA GAT GTA CAG GGG      822
Arg Met Ile Ala Asp Lys Leu Glu Val Ser Pro Arg Asp Val Gln Gly
                170                 175                 180

ATG GTC ATA GGT GTA CAC GGC GAT CAT ATG GTG CCC CTA AGT AGA TAT      870
Met Val Ile Gly Val His Gly Asp His Met Val Pro Leu Ser Arg Tyr
                185                 190                 195

GCA ACA GTT AAC GGC ATC CCG CTT TCT GAG TTT GTT AAG AAG GGC TGG      918
Ala Thr Val Asn Gly Ile Pro Leu Ser Glu Phe Val Lys Lys Gly Trp
                200                 205                 210

ATC AAG CAA GAA GAA GTA GAT GAT ATC GTT CAG AAG ACC AAG GTC GCT      966
Ile Lys Gln Glu Glu Val Asp Asp Ile Val Gln Lys Thr Lys Val Ala
                215                 220                 225

GGA GGA GAG ATC GTA CGC CTA TTA GGA CAA GGC TCT GCT TAC TAT GCT     1014
Gly Gly Glu Ile Val Arg Leu Leu Gly Gln Gly Ser Ala Tyr Tyr Ala
230                 235                 240                 245

CCA GGG GCT TCA GCT ATT CAG ATG GCT GAG AGC TAT CTA AAG GAT AGA     1062
Pro Gly Ala Ser Ala Ile Gln Met Ala Glu Ser Tyr Leu Lys Asp Arg
                250                 255                 260

AAG AGA GTG ATG GTT TGC TCT TGC TAC TTG CAA GGA CAA TAT GGT GTA     1110
Lys Arg Val Met Val Cys Ser Cys Tyr Leu Gln Gly Gln Tyr Gly Val
                265                 270                 275

CAG AAT CAC TAC TTA GGA GTA CCT TGT GTT ATC GGT GGG AGA GGT GTT     1158
Gln Asn His Tyr Leu Gly Val Pro Cys Val Ile Gly Gly Arg Gly Val
                280                 285                 290

GAG AAG ATT ATT GAG TTA GAA TTG ACC GCA CAA GAA AGA CAG GAG CTT     1206
Glu Lys Ile Ile Glu Leu Glu Leu Thr Ala Gln Glu Arg Gln Glu Leu
                295                 300                 305

CAG GGA TCT ATC GAT GAG GTT AAG GAG ATG CAG AAG GCT ATT GCT GCT     1254
Gln Gly Ser Ile Asp Glu Val Lys Glu Met Gln Lys Ala Ile Ala Ala
310                 315                 320                 325

CTT GAT GCA TCC AAG TAAGCAGCAG CAAAATCGCA GAAGTTGCAG CGCTAGAACA     1309
Leu Asp Ala Ser Lys
                330

ACCAGCAGCA GCAGCAGCAG CAGCCTATAG TTCTTGCTGC TGCTGTTCCT ACTACAGCTG   1369

CGGCTTTCTT CCTCGTGTTA TTATCATGAT AGTAAGCTGC TGTACCAGCA GCAGCAGCAG   1429

CAGCAGATTT TGCTTGCACC GCCGTTTGTT TTGCGTACAC CGGCAGAAAT ATTGACTTGC   1489

AGTTAGGAGA AAGAAAGAAA ACAAACACGA TCCCATCGAT CCCAATAAAC CCCACACTGT   1549

CGATCCCATC GATCCCAGCA ACTCCACGGG GCTCTTAACT GTTAAACCTA TTATTCTTAT   1609

CATTACTGTC TCCCGAATTC GATATCAAGC TTATCGATAC CGTCGACCTC GAGGGGGGGC   1669

CCGGTACCCA                                                         1679

(2) INFORMATION FOR SEQ ID NO: 2:

(i) SEQUENCE CHARACTERISTICS:
        (A) LENGTH: 330 amino acids
        (B) TYPE: amino acid
        (D) TOPOLOGY: linear (ii) MOLECULE TYPE: protein
```

-continued (xi) SEQUENCE DESCRIPTION: SEQ ID NO: 2:

```
Met Ala Val Phe Glu Lys Asn Thr Arg Pro Lys Ile Ala Met Val Gly
 1               5                  10                  15

Ser Gly Met Ile Gly Gly Thr Met Ala Phe Leu Cys Ser Leu Arg Glu
                20                  25                  30

Leu Gly Asp Val Val Leu Phe Asp Val Val Pro Asn Met Pro Met Gly
            35                  40                  45

Lys Ala Met Asp Ile Ser His Asn Ser Ser Val Val Asp Thr Gly Ile
        50                  55                  60

Thr Val Tyr Gly Ser Asn Ser Tyr Glu Cys Leu Lys Gly Ala Asp Val
 65                 70                  75                  80

Val Ile Ile Thr Ala Gly Ile Thr Lys Ile Pro Gly Lys Ser Asp Lys
                85                  90                  95

Glu Trp Ser Arg Met Asp Leu Leu Pro Val Asn Ile Lys Ile Met Arg
                100                 105                 110

Glu Val Gly Ala Ala Ile Lys Ser Tyr Cys Pro Asn Ala Phe Val Ile
            115                 120                 125

Asn Ile Thr Asn Pro Leu Asp Val Met Val Ala Ala Leu Gln Glu Ser
    130                 135                 140

Ser Gly Leu Pro His His Arg Ile Cys Gly Met Ala Gly Met Leu Asp
145                 150                 155                 160

Ser Ser Arg Phe Arg Arg Met Ile Ala Asp Lys Leu Glu Val Ser Pro
                165                 170                 175

Arg Asp Val Gln Gly Met Val Ile Gly Val His Gly Asp His Met Val
                180                 185                 190

Pro Leu Ser Arg Tyr Ala Thr Val Asn Gly Ile Pro Leu Ser Glu Phe
            195                 200                 205

Val Lys Lys Gly Trp Ile Lys Gln Glu Glu Val Asp Asp Ile Val Gln
    210                 215                 220

Lys Thr Lys Val Ala Gly Gly Glu Ile Val Arg Leu Leu Gly Gln Gly
225                 230                 235                 240

Ser Ala Tyr Tyr Ala Pro Gly Ala Ser Ala Ile Gln Met Ala Glu Ser
                245                 250                 255

Tyr Leu Lys Asp Arg Lys Arg Val Met Val Cys Ser Cys Tyr Leu Gln
            260                 265                 270

Gly Gln Tyr Gly Val Gln Asn His Tyr Leu Gly Val Pro Cys Val Ile
        275                 280                 285

Gly Gly Arg Gly Val Glu Lys Ile Ile Glu Leu Glu Leu Thr Ala Gln
    290                 295                 300

Glu Arg Gln Glu Leu Gln Gly Ser Ile Asp Glu Val Lys Glu Met Gln
305                 310                 315                 320

Lys Ala Ile Ala Ala Leu Asp Ala Ser Lys
                325                 330
``` we claim:

1. An isolated nucleic acid molecule comprising a nucleic acid sequence encoding an immunogenic fragment of Eimeria lactate dehydrogenase (LDH), wherein said LDH is one that will immunologically react with antiserum raised against the LDH of SEQ ID NO: 2.

2. The nucleic acid molecule of claim 1, which comprises the DNA sequence of SEQ ID NO: 1.

3. The nucleic acid molecule of claim 1, which comprises expression control sequences in operable linkage with the nucleic acid sequence encoding an immunogenic fragment of Eimeria lactate dehydrogenase (LDH) for expression of said nucleic acid sequence.

4. A vector which comprises the nucleic acid molecule of claim 1.

5. A vector which comprises the nucleic acid molecule of claim 3.

6. An isolated host cell comprising the nucleic acid molecule of claim 1.

7. A process for producing an immunogenic fragment of Eimeria lactate dehydrogenase (LDH) comprising, culturing the host cell of claim 6 such that the nucleic acid sequence is expressed at a level sufficient for the production of an immunogenic fragment of Eimeria lactate dehydrogenase (LDH).

8. A process for the preparation of a coccidiosis vaccine comprising, culturing the host cell of claim 6, collecting the vector, and formulating said vector into a pharmaceutical composition.

9. An isolated host cell comprising the vector of claim 4.

10. An isolated host cell comprising the vector of claim 5.

11. A vaccine for protection of poultry against coccidiosis, which comprises the nucleic acid molecule of claim 3, and a pharmaceutically acceptable carrier.

12. A vaccine for protection of poultry against coccidiosis, which comprises the vector of claim 4, and a pharmaceutically acceptable carrier.

13. A vaccine for protection of poultry against coccidiosis, which comprises the host cell of claim 6, and a pharmaceutically acceptable carrier.

14. A vaccine for protection of poultry against coccidiosis, which comprises the host cell of claim 9, and a pharmaceutically acceptable carrier.

15. A vaccine for protection of poultry against coccidiosis, which comprises the host cell of claim 10, and a pharmaceutically acceptable carrier.

16. A method for the protection of poultry against coccidiosis comprising, administering to the poultry the vaccine of claim 11, wherein the nucleic acid sequence of said vaccine is expressed at a level sufficient for protection of said poultry against coccidiosis.

17. A method for the protection of poultry against coccidiosis comprising, administering to the poultry the vaccine of claim 12, wherein the nucleic acid sequence of said vaccine is expressed at a level sufficient for protection of said poultry against coccidiosis.

18. A method for the protection of poultry against coccidiosis, comprising administering to the poultry the vaccine of claim 13, wherein the nucleic acid sequence of said vaccine is expressed at a level sufficient for protection of said poultry against coccidiosis.

19. A method for the protection of poultry against coccidiosis, comprising administering to the poultry the vaccine of claim 14, wherein the nucleic acid sequence of said vaccine is expressed at a level sufficient for protection of said poultry against coccidiosis.

20. A method for the protection of poultry against coccidiosis, comprising administering to the poultry the vaccine of claim 15, wherein the nucleic acid sequence of said vaccine is expressed at a level sufficient for protection of said poultry against coccidiosis.

21. The nucleic acid molecule of claim 1, wherein said nucleic acid sequence encodes Eimeria lactate dehydrogenase (LDH).

22. The nucleic acid molecule of claim 1, wherein said nucleic acid sequence encodes the amino acid sequence of SEQ ID NO: 2.

23. An isolated nucleic acid molecule comprising a nucleic acid sequence encoding an immunogenic fragment of the amino acid sequence of SEQ ID NO: 2.

24. An isolated nucleic acid molecule comprising a nucleic acid sequence encoding the amino acid sequence of SEQ ID NO: 2.

25. A vaccine for protection of poultry against coccidiosis, which comprises the vector of claim 5, and a pharmaceutically acceptable carrier.

* * * * *